United States Patent
Dodd et al.

(10) Patent No.: US 9,284,523 B2
(45) Date of Patent: Mar. 15, 2016

(54) PREMOUNTED FLUID CONVEYANCE ASSEMBLY FOR CELL EXPANSION SYSTEM AND METHOD OF USE ASSOCIATED THEREWITH

(75) Inventors: Jon A. Dodd, Littleton, CO (US); Thomas G. Dilorenzo, Aravada, CO (US); Frank Corbin, III, Littleton, CO (US); Glen Delbert Antwiler, Lakewood, CO (US)

(73) Assignee: Terumo BCT, Inc., Lakewood, CO (US)

( * ) Notice: Subject to any disclaimer, the term of this patent is extended or adjusted under 35 U.S.C. 154(b) by 672 days.

(21) Appl. No.: 12/606,064

(22) Filed: Oct. 26, 2009

(65) Prior Publication Data

US 2010/0105138 A1 Apr. 29, 2010

Related U.S. Application Data

(60) Provisional application No. 61/108,773, filed on Oct. 27, 2008, provisional application No. 61/153,583, filed on Feb. 18, 2009.

(51) Int. Cl.
*C12M 1/00* (2006.01)
*C12M 3/00* (2006.01)
*C12M 1/12* (2006.01)

(52) U.S. Cl.
CPC .............. *C12M 23/48* (2013.01); *C12M 23/42* (2013.01); *C12M 25/10* (2013.01); *C12M 25/12* (2013.01)

(58) Field of Classification Search
CPC ...... C12M 27/10; C12M 23/06; C12M 23/44; C12M 23/40; C12M 23/48
See application file for complete search history.

(56) References Cited

U.S. PATENT DOCUMENTS 4,231,366 A 11/1980 Schael
4,388,944 A 6/1983 Honma et al.
(Continued)

FOREIGN PATENT DOCUMENTS

WO 97/14962 4/1997
WO 99/57561 A2 11/1999
(Continued)

OTHER PUBLICATIONS

International Search Report dated Feb. 3, 2010, issued in PCT Application No. PCT/US2009/062213.
(Continued)

*Primary Examiner* — Nathan Bowers
(74) *Attorney, Agent, or Firm* — René A. Pereyra; John R. Merkling; Elizabeth J. Reagan

(57) ABSTRACT

A premounted fluid conveyance assembly for use with a cell expansion machine comprises a tubing-organizer and a fluid conveyance system. The fluid conveyance system is at least partially attached to the tubing-organizer, and the fluid conveyance system comprises an oxygenator or gas transfer module, a length of tubing and a bioreactor all fluidly interconnected. The premounted fluid conveyance assembly is adapted to be detachably-attached to the cell expansion machine. Accordingly, after a premounted fluid conveyance assembly is used, it is removed from the cell expansion machine by disengaging it from the cell expansion machine. Thereafter, another premounted fluid conveyance assembly can be attached in place of the previously used premounted fluid conveyance assembly.

13 Claims, 11 Drawing Sheets

(56) References Cited

U.S. PATENT DOCUMENTS

| | | | |
|---|---|---|---|
| 4,436,620 | A | 3/1984 | Bellotti et al. |
| 4,798,090 | A | 1/1989 | Heath et al. |
| 4,918,019 | A | 4/1990 | Guinn |
| 4,976,708 | A | 12/1990 | Oshiyama |
| 4,997,464 | A | 3/1991 | Kopf |
| 5,026,650 | A | 6/1991 | Schwarz et al. |
| 5,126,238 | A | 6/1992 | Gebhard et al. |
| 5,153,133 | A * | 10/1992 | Schwarz et al. ............. 435/401 |
| 5,162,225 | A | 11/1992 | Sager et al. |
| 5,178,603 | A | 1/1993 | Prince |
| 5,202,254 | A | 4/1993 | Amiot et al. |
| 5,316,905 | A | 5/1994 | Mori et al. |
| 5,424,209 | A | 6/1995 | Kearney |
| 5,958,763 | A | 9/1999 | Goffe |
| 5,985,653 | A | 11/1999 | Armstrong et al. |
| 6,001,585 | A | 12/1999 | Gramer |
| 6,048,721 | A | 4/2000 | Armstrong et al. |
| 6,096,532 | A | 8/2000 | Armstrong et al. |
| 6,228,635 | B1 | 5/2001 | Armstrong et al. |
| 6,238,908 | B1 | 5/2001 | Armstrong et al. |
| 7,270,996 | B2 | 9/2007 | Cannon et al. |
| 7,855,070 | B2 | 12/2010 | Vukasinovic et al. |
| 7,892,332 | B2 | 2/2011 | Prisco et al. |
| 8,109,284 | B2 | 2/2012 | Furey et al. |
| 8,895,291 | B2 | 11/2014 | DiLorenzo et al. |
| 2003/0037836 | A1 | 2/2003 | Blatt et al. |
| 2004/0221719 | A1 | 11/2004 | Wright et al. |
| 2004/0235142 | A1* | 11/2004 | Schein et al. ............. 435/284.1 |
| 2005/0239198 | A1* | 10/2005 | Kunas et al. ............. 435/297.1 |
| 2006/0137663 | A1 | 6/2006 | Vaught |
| 2008/0032398 | A1 | 2/2008 | Cannon et al. |
| 2008/0145925 | A1* | 6/2008 | Sakai et al. ............. 435/297.2 |
| 2008/0220523 | A1 | 9/2008 | Antwiler |
| 2011/0155256 | A1 | 6/2011 | DiLorenzo et al. |

FOREIGN PATENT DOCUMENTS

| | | |
|---|---|---|
| WO | 2005/011569 A2 | 2/2005 |
| WO | 2007/136821 | 11/2007 |
| WO | 2007/139742 | 12/2007 |
| WO | 2007/139746 | 12/2007 |
| WO | 2007/139747 | 12/2007 |
| WO | 2007/139748 | 12/2007 |
| WO | 2008/109200 | 9/2008 |
| WO | 2008/109674 | 9/2008 |
| WO | 2008/112845 | 9/2008 |
| WO | 2008/128165 | 10/2008 |

OTHER PUBLICATIONS

Written Opinion dated Feb. 3, 2010, issued in PCT Application No. PCT/US2009/062213.
Office Action, Japanese Patent Application No. 2001-533424, Nov. 8, 2013 (English language translation included).
International Search Report and Written Opinion, PCT/US2011/027765, Jul. 11, 2011.
International Search Report and Written Opinion, PCT/US2011/055482, Jun. 21, 2012.
Office Action, U.S. Appl. No. 13/043,933, Mar. 21, 2013.
Office Action, U.S. Appl. No. 13/043,933, Aug. 23, 2013.
Notice of Allowance and Fee(s) Due, U.S. Appl. No. 13/043,933, May 28, 2014.
Requirement for Restriction/Election, U.S. Appl. No. 13/269,512, Aug. 16, 2013.
Office Action, U.S. Appl. No. 13/269,512, Oct. 17, 2013.
Notice of Allowance and Fee(s) Due, U.S. Appl. No. 13/269,512, Sep. 15, 2014.
Patent Examination Report No. 1, Australian Patent Application No. 2009320165, Jul. 10, 2014.
Communication Pursuant to Article 93(3) EPC, European Patent Application No. 09752942.4, Mar. 31, 2015.
Office Action, U.S. Appl. No. 14/548,617, Apr. 13, 2015.
Notice of Allowance and Fee(s) Due, U.S. Appl. No. 13/043,933, Dec. 10, 2014.
Office Action, U.S. Appl. No. 14/548,617, Aug. 27, 2015.
Office Action, Japanese Patent Application No. 2001-533424, Sep. 2, 2014 (English language translation included).
Office Action, U.S. Appl. No. 14/548,617, Jan. 5, 2016.

* cited by examiner

PREMOUNTED FLUID CONVEYANCE ASSEMBLY FOR CELL EXPANSION SYSTEM AND METHOD OF USE ASSOCIATED THEREWITH

CROSS REFERENCE TO RELATED APPLICATIONS

The present application claims the benefit of U.S. Patent Provisional Patent Application Ser. No. 61/108,773 filed on Oct. 27, 2008, and U.S. Patent Provisional Patent Application Ser. No. 61/153,583 filed on Feb. 18, 2009, the contents of which are incorporated herein by reference in their entirety.

FIELD

The present disclosure relates to an assembly of mounted elements that can be easily attached to a cell expansion machine forming part of a cell expansion system (CES) that is used to grow cells.

BACKGROUND

CESs are used to expand and differentiate cells. Cell expansion systems are known in the art. For example, U.S. Pat. Nos. 5,162,225 and 6,001,585 generally describe cell expansion systems designed for cell expansion.

The potential use of stem cells in a variety of treatments and therapies has achieved particular attention. Cell expansion systems can be used to grow stem cells, as well as other types of cells, such as bone marrow cells. Stem cells which are expanded from donor cells can be used to repair or replace damaged or defective tissues and have broad clinical applications for a wide range of diseases. Recent advances in the regenerative medicine field demonstrate that stem cells have properties such as proliferation and self-renewal capacity, maintenance of the unspecialized state, and the ability to differentiate into specialized cells under particular conditions.

Limiting factors associated with performing cell expansion include the sterility of elements associated with the cell expansion system and the ability of lab technicians to timely disassemble equipment associated with performing a first cell expansion followed by subsequently setting up equipment associated with performing a subsequent cell expansion. Accordingly, there is a need for an assembly and methods associated with the assembly that enable a lab technician to prepare, with relatively limited downtime, equipment necessary to conduct a second cell expansion after a first cell expansion. The present disclosure addresses these and other needs.

SUMMARY

It is to be understood that the present invention includes a variety of different versions or embodiments, and this Summary is not meant to be limiting or all-inclusive. This Summary provides some general descriptions of some of the embodiments, but may also include some more specific descriptions of other embodiments.

Interchangeability of fluid conveyance elements is achieved by providing a premounted fluid conveyance assembly for use with a cell expansion machine. Accordingly, in at least one embodiment a premounted fluid conveyance assembly for use with a cell expansion machine is provided, the cell expansion machine including a rotatable shaft, the premounted fluid conveyance assembly comprising:

a tubing-organizer; and
a fluid conveyance system at least partially attached to the tubing-organizer, the fluid conveyance system comprising:
a gas transfer module;
a length of tubing fluidly associated with the gas transfer module; and
a bioreactor fluidly associated with the length of tubing and the gas transfer module;
wherein the tubing-organizer and the fluid conveyance system are adapted to be detachably-attached to the cell expansion machine.

In at least one embodiment, the tubing-organizer comprises a plurality of apertures and a plurality of tubing holders spaced across a height and a width of a wall and a perimeter of the tubing-organizer. In at least one embodiment, at least one aperture of the plurality of apertures comprises an oblong-shaped shaft access aperture adapted for engaging the cell expansion machine and the rotatable shaft.

Cell expansion machines may include a number of valves for controlling fluid flow associated with a cell expansion process. Accordingly, in at least one embodiment, a premounted fluid conveyance assembly for use with a cell expansion machine is provided, the cell expansion machine including at least one valve clamp and a rotatable shaft, the premounted fluid conveyance assembly comprising:

a fluid conveyance system comprising:
a gas transfer module;
a length of tubing fluidly associated with the gas transfer module; and
a bioreactor fluidly associated with the length of tubing and the gas transfer module; and
a support member including a plurality of holding elements, the plurality of holding elements including a gas transfer module mounting post and a plurality of tubing guides holding at least a portion of the length of tubing, wherein the support member further comprises a shaft access aperture for allowing engagement of the bioreactor with the rotatable shaft of the cell expansion machine;
wherein the support member and the fluid conveyance system are adapted to be detachably-attached to the cell expansion machine.

In at least one embodiment, the support member comprises a valve access opening adapted for allowing contact of the at least one valve clamp with a portion of the length of tubing.

In at least one embodiment, a plurality of tubing guide slots are provided for guiding tubing between a back portion and a door of the cell expansion machine. The plurality of tubing guide slots assist with limiting or preventing pinching of the tubing when the closable door is closed against the back portion of the cell expansion machine.

Embodiments of the present invention further include one or more methods associated with using a premounted fluid conveyance assembly. Accordingly, a method of expanding cells using a cell expansion machine is provided, the method comprising;

providing a first detachably-attachable premounted fluid conveyance assembly, the first detachably-attachable premounted fluid conveyance assembly including a fluid conveyance system, wherein portions of the fluid conveyance system are mounted on a support backing, wherein the fluid conveyance system includes fluid conveyance conduit, a gas transfer module, and a bioreactor; and detachably-attaching the support backing of the first detachably-attachable premounted fluid conveyance assembly to the cell expansion machine.

In at least one embodiment, the method may further comprise removing the first detachably-attachable premounted fluid conveyance assembly from a sterile package before detachably-attaching the support backing of the first detachably-attachable premounted fluid conveyance assembly to the cell expansion machine. In at least one embodiment, the method may further comprise causing a fluid flow through at least a portion of the fluid conveyance system including into a rotatable bioreactor of the fluid conveyance system. In at least one embodiment, the method may further comprise rotating the rotatable bioreactor after detachably-attaching the support backing to the cell expansion machine. In at least one embodiment, the method may further comprise detaching the support backing of the first detachably-attachable premounted fluid conveyance assembly from the cell expansion machine, and then attaching a second detachably-attachable premounted fluid conveyance assembly to the cell expansion machine. In at least one embodiment, the cell expansion machine is not sterilized in between detaching the support backing of first detachably-attachable premounted fluid conveyance assembly from the cell expansion machine and attaching a second detachably-attachable premounted fluid conveyance assembly to the cell expansion machine. In at least one embodiment, a fluid volume needed to prime the fluid conveyance system of the first detachably-attachable premounted fluid conveyance is substantially equal to a fluid volume needed to prime the second detachably-attachable premounted fluid conveyance assembly. In at least one embodiment, the method further comprises expanding and harvesting a plurality of cells from the cell expansion machine without sterilizing the cell expansion machine.

Various components are referred to herein as "operably associated." As used herein, "operably associated" refers to components that are linked together in operable fashion, and encompasses embodiments in which components are linked directly, as well as embodiments in which additional components are placed between the two linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected.

Generally, any kind of fluid, including buffers, protein-containing fluid, and cell-containing fluid can flow through the various circulation paths, inlet paths, and outlet paths. As used herein, "fluid," "media," and "fluid media" are used interchangeably.

As used herein, the term "detachably-attached" means temporarily attached, and "detachably-attachable" means adapted to be temporarily attached.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Summary does not contain all of the aspects and embodiments of the one or more present inventions, is not meant to be limiting or restrictive in any manner, and that the invention(s) as disclosed herein is/are understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

To further clarify the above and other advantages and features of the present invention, a more particular description of the invention is rendered by reference to specific embodiments thereof which are illustrated in the appended drawings. It should be appreciated that these drawings depict only typical embodiments of the invention and are therefore not to be considered limiting of its scope. The invention is described and explained with additional specificity and detail through the use of the accompanying drawings in which.

The drawings are not necessarily to scale.

DETAILED DESCRIPTION

The present disclosure is generally directed to a premounted fluid conveyance assembly for use with a cell expansion machine, wherein the premounted fluid conveyance assembly and the cell expansion machine form at least a portion of a cell expansion system. As described below, a fluid conveyance system is at least partially attached to a tubing-organizer. The fluid conveyance system comprises a number of elements, including a gas transfer module, fluid conduit (e.g., tubing), and a bioreactor. The tubing-organizer and the fluid conveyance system are an integrated unit serving as a premounted fluid conveyance assembly that is adapted to be detachably-attached to the cell expansion machine.

Figure 1:
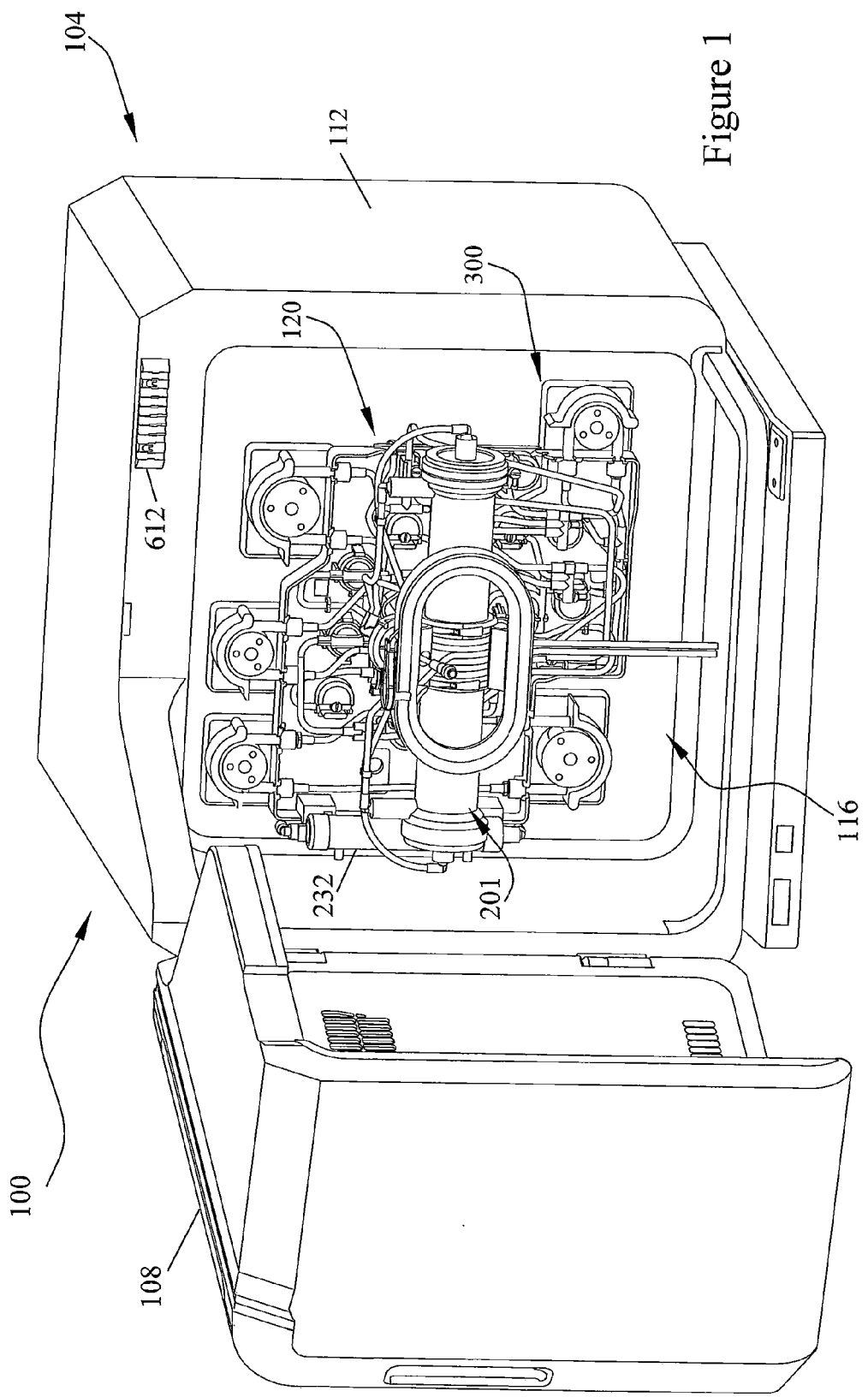
FIG. 1 is a perspective view of a cell expansion system including an embodiment of a premounted fluid conveyance assembly.

With reference now to FIG. 1, an embodiment of a CES 100 is shown. The CES 100 includes a cell expansion machine 104 that comprises a hatch or closable door 108 for engagement with a back portion 112 of the cell expansion machine 104. An interior space 116 within the cell expansion machine 104 includes features adapted for receiving and engaging a premounted fluid conveyance assembly 120. As described in detail below, the premounted fluid conveyance assembly 120 is detachably-attachable to the cell expansion machine 104 to facilitate relatively quick exchange of a new or unused premounted fluid conveyance assembly 120 at a cell expansion machine 104 for a used premounted fluid conveyance assembly 120 at the same cell expansion machine 104. Advantageously, a single cell expansion machine 104 can be operated to grow or expand a first set of cells using a first premounted fluid conveyance assembly 120, and thereafter, used to grow or expand a second set of cells using a second premounted fluid conveyance assembly 120 without needing to be sanitized between interchanging the first premounted fluid conveyance assembly 120 for the second premounted fluid conveyance assembly 120.

Figure 2:
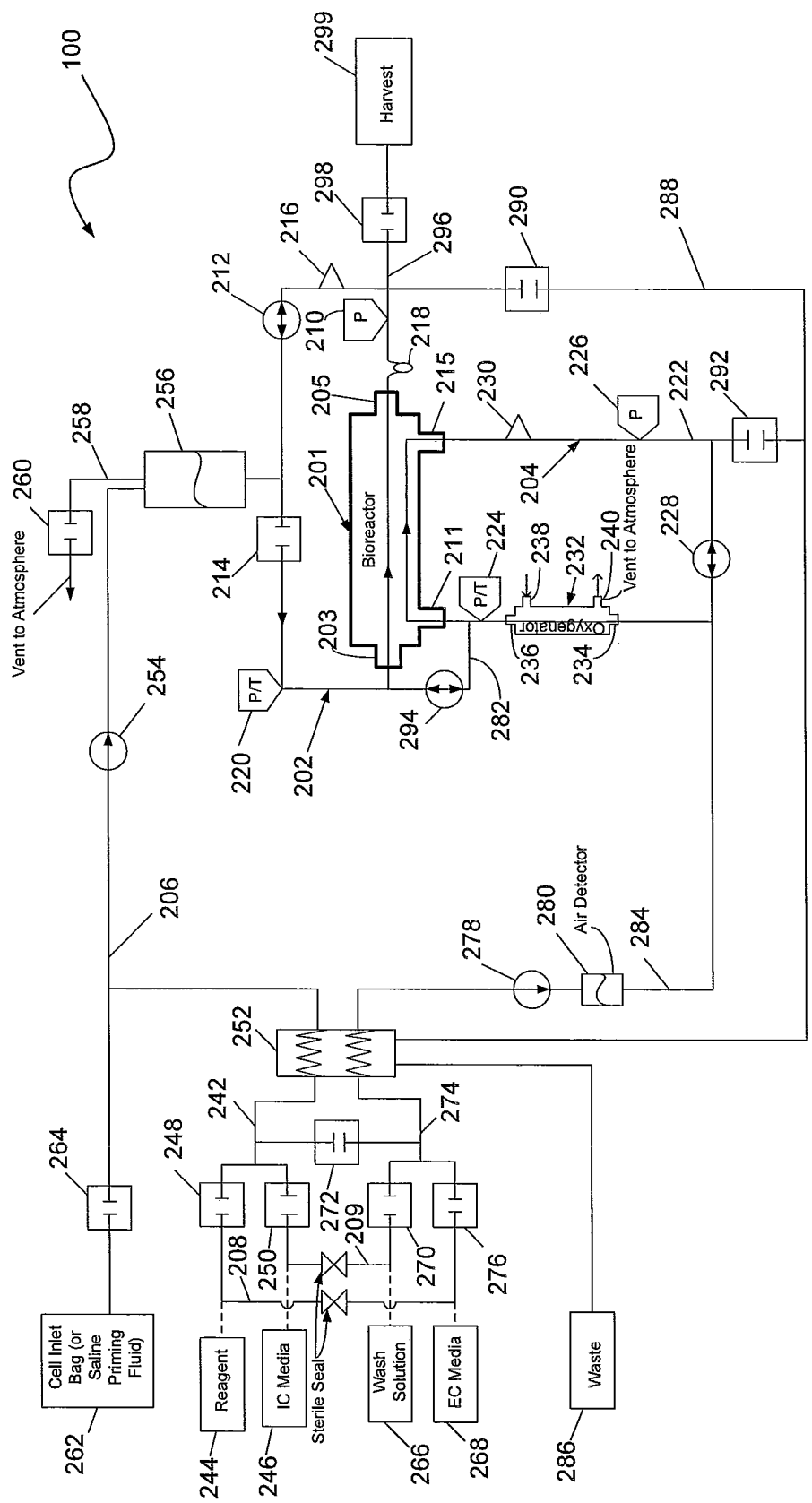
FIG. 2 is a schematic of an embodiment of a cell expansion system.

Referring now to FIG. 2, a schematic of one possible embodiment of a CES is shown. CES 100 includes first fluid circulation path 202 (also referred to as the "intracapillary loop" or "IC loop") and second fluid circulation path 204 (also referred to as the "extracapillary loop" or "EC loop"). First fluid flow path 206 is fluidly associated with bioreactor 201 to form the first fluid circulation path 202. Fluid flows into bioreactor 201 through IC inlet port 203, through hollow fibers in bioreactor 201, and exits via IC outlet port 205.

Fluid entering bioreactor via the EC inlet port 211 is in contact with the outside of the hollow fibers. Small molecules (e.g., water, oxygen, lactate, etc.) can diffuse through the hollow fibers from the interior of the hollow fiber to the EC space, or from the EC space to the IC space. Large molecular weight molecules such as growth factors are typically too large to pass through the hollow fiber membrane, and remain in the IC space of the hollow fibers. Cells can be contained within the first circulation path and/or second circulation path, and can be on either the IC side and/or EC side of the membrane.

Although bioreactor 201 is depicted as cylindrical in shape, it could have a variety of shapes, such as a rectangular cube. The bioreactor 201 can be made of any type of biocompatible polymeric material, including a substantially transparent material that permits an observer to see into the bioreactor 201. By way of example and not limitation, specifications for an exemplary bioreactor 201 for use in a CES 100 are provided in the following table.

TABLE 1

| Specifications for an Exemplary Bioreactor (BioR17A Bioreactor) | | |
| --- | --- | --- |
| 11520 | fibers | fiber count in bioreactor |
| $215 \times 10^{-6}$ | m | fiber ID |

Referring still to FIG. 2, pressure gauge 210 measures the pressure of media leaving bioreactor 201. Media flows through IC circulation pump 212 which can be used to control the rate of media flow. Media then flows through valve 214. As those skilled in the art will appreciate, additional valves and/or other devices can be placed at various locations to isolate and/or measure characteristics of the media along portions of the fluid paths. Accordingly, it is to be understood that the schematic shown represents one possible configuration for various elements of the CES and modifications to the schematic shown are within the scope of the one or more present inventions.

With regard to the IC loop, samples of media can be obtained from sample port 216 or sample coil 218 during operation. Pressure/temperature gauge 220 disposed in first fluid circulation path 202 allows detection of media pressure and temperature during operation. Media then returns to IC inlet port 203 to complete fluid circulation path 202. Cells grown/expanded in bioreactor 201 can be flushed out of bioreactor 201 or redistributed within hollow fibers for further growth.

Second fluid circulation path 204 includes second fluid flow path 222 that is fluidly associated with bioreactor 201 in a loop. Fluid in second fluid circulation path 204 enters bioreactor 201 via EC inlet port 211, and leaves bioreactor 201 via EC outlet port 215. Media is in contact with the outside of the hollow fibers in the bioreactor 201, thereby allowing diffusion of small molecules into and out of the hollow fibers.

Pressure/temperature gauge 224 disposed in the second fluid circulation path 204 allows the pressure and temperature of media to be measured before the media enters the EC space of the bioreactor 201. Pressure gauge 226 allows the pressure of media in the second fluid circulation path 204 to be measured after it leaves the bioreactor 201. With regard to the EC loop, samples of media can be obtained from sample port 230 during operation.

After leaving EC outlet port 215 of bioreactor 201, fluid in second fluid circulation path 204 passes through EC circulation pump 228 to gas transfer module or oxygenator 232. Second fluid flow path 222 is fluidly associated with oxygenator 232 via oxygenator inlet port 234 and oxygenator outlet port 236. In operation, fluid media flows into oxygenator 232 via oxygenator inlet port 234, and exits oxygenator 232 via oxygenator outlet port 236.

The gas transfer module or oxygenator 232 adds oxygen to and removes bubbles from media in the CES. In various embodiments, media in second fluid circulation path 204 is in equilibrium with gas entering oxygenator 232. The oxygenator 232 can be any appropriately sized oxygenator known in the art. Air or gas flows into oxygenator 232 via filter 238 and out of oxygenator 232 through filter 240. Filters 238 and 240 reduce or prevent contamination of oxygenator 232 and associated media. Air or gas vented from the CES 100 can pass to the atmosphere via the oxygenator 232.

In accordance with at least one embodiment, cells and fluid media can be introduced to fluid circulation path 202 via first fluid inlet path 242. Fluid container 244 (e.g., Reagent) and fluid container 246 (e.g., IC Media) are fluidly associated with first fluid inlet path 242 via valves 248 and 250, respectively. Cells and fluid proceed through heat exchanger 252 (if used), IC inlet pump 254, and into air removal chamber 256. Air removal chamber 256 is fluidly associated with first circulation path 202. Air or gas vented from the CES 100 can pass to the atmosphere out air valve 260 via line 258 that is fluidly associated with air removal chamber 256.

Fluid container 262 (e.g., Cell Inlet Bag (or Saline Priming Fluid)) is fluidly associated with the first fluid circulation path 202 via valve 264. Additional fluid can be added to first or second fluid circulation paths 202 and 204 from fluid container 266 (e.g., Wash Solution) and fluid container 268 (e.g., EC Media). Fluid container 266 is fluidly associated with valve 270 that is fluidly associated with first fluid circulation path 202 via distribution valve 272 and first fluid inlet path 242. Alternatively, fluid container 266 can be fluidly associated with second fluid inlet path 274 by opening valve 270 and closing distribution valve 272. Likewise, fluid container 268 is fluidly associated with valve 276, that is fluidly associated with first fluid circulation path 202 via first fluid inlet path 242. Alternatively, fluid container 268 is fluidly associated with second fluid inlet path 274 by opening valve 276 and closing valve distribution 272.

In the IC loop, fluid is initially advanced by the IC inlet pump 254. In the EC loop, fluid is initially advanced by the EC inlet pump 278. An air detector 280, such as an ultrasonic sensor, may be associated with the EC inlet path 284.

In at least one embodiment, first and second fluid circulation paths 202 and 204 are connected to waste line 288. When valve 290 is opened, IC media can flow through waste line 288 that leads to the heat exchanger 252 and then to waste bag 286. Likewise, when valve 292 is opened, EC media can flow through waste line 288 that leads to the heat exchanger 252 and then to waste bag 286. The heat exchanger 252 serves to recover heat from the waste line 288 and make such heat available for heating fluids entering via the first or second fluid inlet paths 242 and 274, respectively.

Cells can be harvested via cell harvest path 296. Here, cells from bioreactor 201 can be harvested by pumping media containing the cells through cell harvest path 296 and valve 298 to cell harvest bag 299. When harvesting cells, or at other times as may be desired, distribution pump 294 can pump media through a connector path 282 located between the first and second fluid circulation paths 202 and 204.

As can be appreciated by those skilled in the art, the fluid paths discussed above and illustrated in FIG. 2 include a number of fluid conduits. To interconnect the fluid conduits and properly associate the fluid conduits to the appropriate valves, pumps, fluid bags and structures could require a lab technician to spend considerable set-up time. Moreover, the cell expansion machine remains essentially idle while the lab technician expends time and effort to disconnect the used fluid conduits, sanitize the cell expansion machine, and then reconnect new or sanitized fluid conduit to the cell expansion machine for a subsequent cell expansion cycle. In accordance with at least one embodiment of the present invention, to expedite such a process, at least some elements of the fluid conveyance system are provided in the form of a sanitized premounted assembly.

Figure 3:
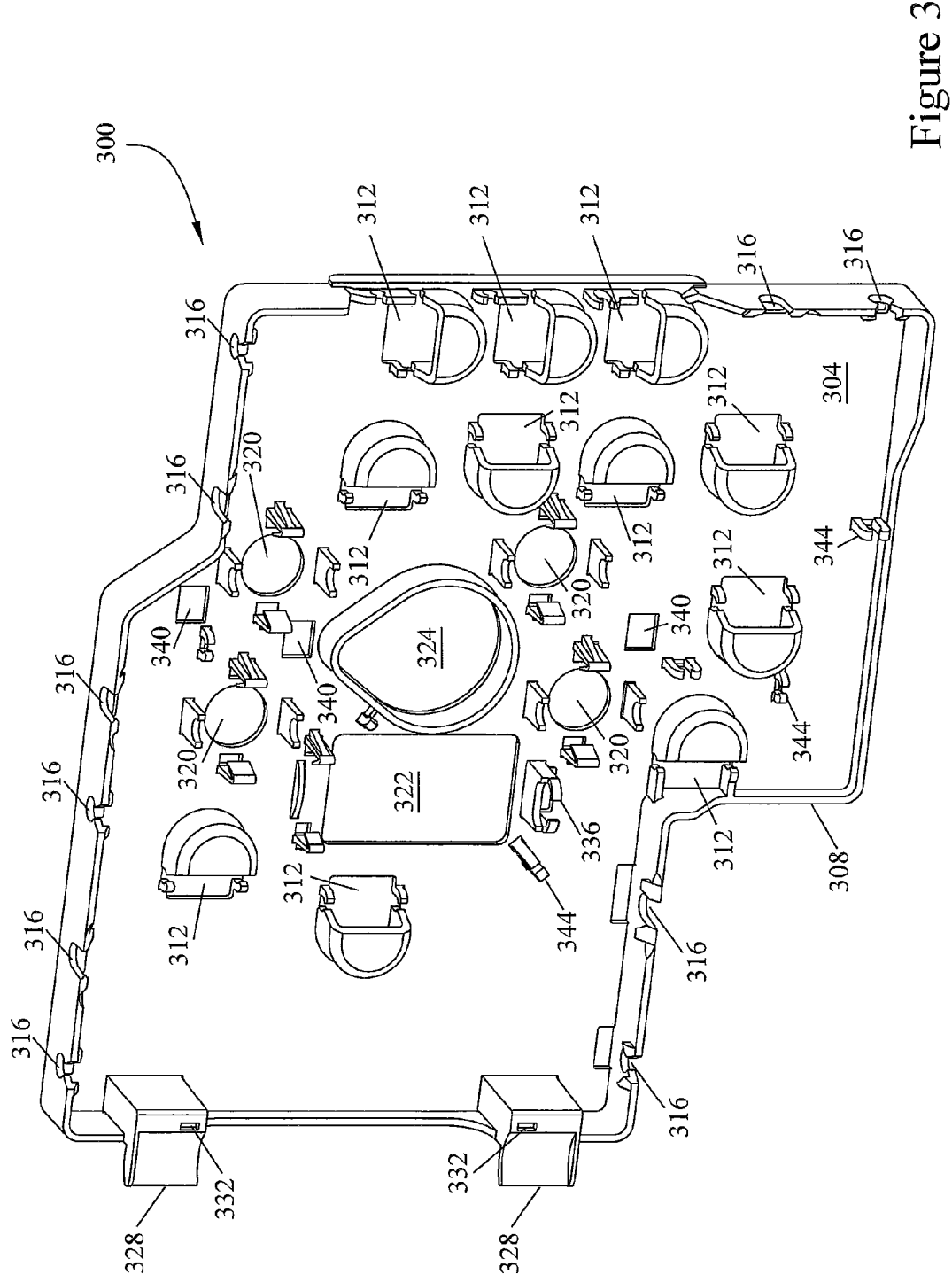
FIG. 3 is a perspective view of an embodiment of a tubing-organizer.

With reference now to FIG. 3, an embodiment of a support member or tubing-organizer 300 is shown. The tubing-organizer 300 includes a wall 304 having a perimeter 308. Residing within the wall 304 or perimeter 308 are a number of features for guiding and/or retaining elements of the fluid conveyance system. More particularly, the tubing-organizer 300 includes a plurality of valve access openings 312 for valves residing on the cell expansion machine 104. In addition, the tubing-organizer 300 also includes a plurality of pump tubing clips 316 along the perimeter 308 to hold tubing to be engaged with pumps on the cell expansion machine 104. The tubing-organizer 300 also includes a plurality of sensor ports 320. The sensor ports 320 provide access, for example, between the pressure and temperatures sensors on the cell expansion machine 104 with the sensor couplings of the fluid conveyance system. Fluid level sensor port 322 provides access through the wall 304 of the tubing-organizer 300 to allow fluid level sensors on the cell expansion machine 104 to read the level of fluid in the air removal chamber 256. The valve access openings 312, pump tubing clips 316 and sensor ports 320 are spaced apart so that the valves, pumps and sensors on the cell expansion machine 104 can engage different portions of the fluid conduit.

Still referring to FIG. 3, the tubing-organizer 300 also includes a shaft access aperture 324 for a shaft (shown in FIG. 6 and discussed below) of the cell expansion machine 104 to detachably engage the bioreactor 201. In addition, the tubing-organizer 300 further includes one or more oxygenator mounting posts 328 for receiving an oxygenator 232. The one or more oxygenator mounting posts 328 may include a fastener port 332 for receiving, by way of example, a zip tie to secure the oxygenator 232 to the oxygenator mounting post 328. The tubing-organizer 300 may further include chamber mounting post 336 for securing the air removal chamber 256. In addition, the tubing-organizer 300 may further include one or more apertures or fasteners 340 for detachably-attaching the tubing-organizer to the cell expansion machine 104. Whether present on the cell expansion machine 104 or the tubing organizer 300, such fasteners may encompass a variety of devices, including, but not limited to screws, bolts, spring-loaded or biased fasteners, movable clips or pins, and similar mechanisms or combinations of the above. The tubing-organizer 300 may further include a variety of other features, including one or more tubing clips 344 to direct tubing.

Figure 4:
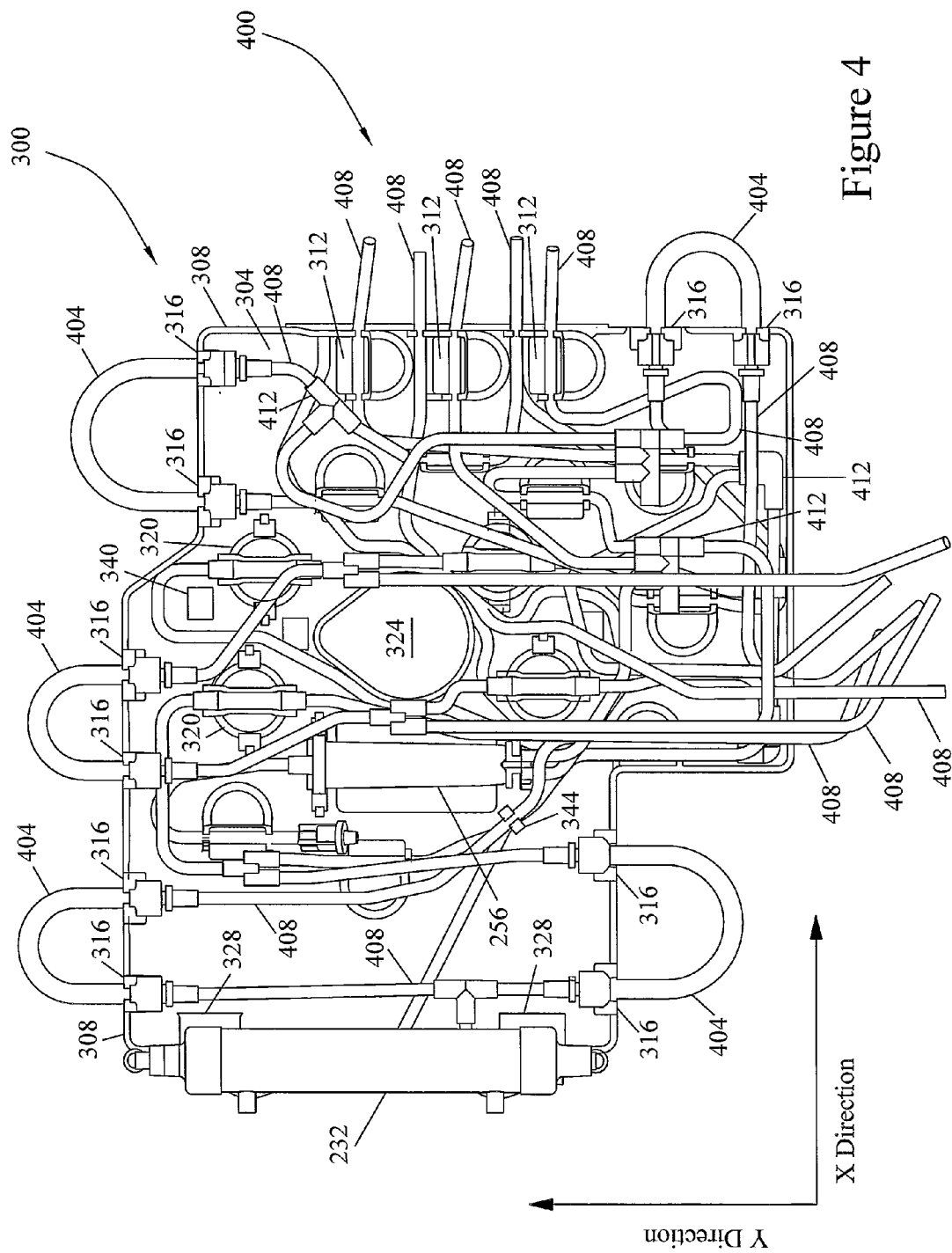
FIG. 4 is a front elevation view of the device shown in FIG. 3 with portions of a fluid conveyance system.

Referring now to FIG. 4, an embodiment of the tubing-organizer 300 is shown with a portion of the fluid conveyance system 400. For clarity, the bioreactor 201 is omitted from FIG. 4. Pump tubing conduit 404 for engaging the various pumps of the cell expansion machine 104 can be seen extending beyond and looping back to the perimeter 308 of the tubing-organizer 300. In addition, tubing 408 can be seen extending between the various valve access openings 312, pump tubing clips 316 and sensor ports 320. As needed, various tubing fittings 412 are used to interconnect sections of tubing 408.

Still referring to FIG. 4, the components of the fluid conveyance system 400 associated with the premounted fluid conveyance assembly 120 are generally distributed across the width and height of the tubing-organizer 300 in the "X" direction and "Y" direction, respectively. Such distribution of the various portions of tubing 408 and other elements of the fluid conveyance system 400 allow a lab technician to engage the premounted fluid conveyance assembly 120 to the cell expansion machine 104 in a relatively short amount of time.

Figure 5:
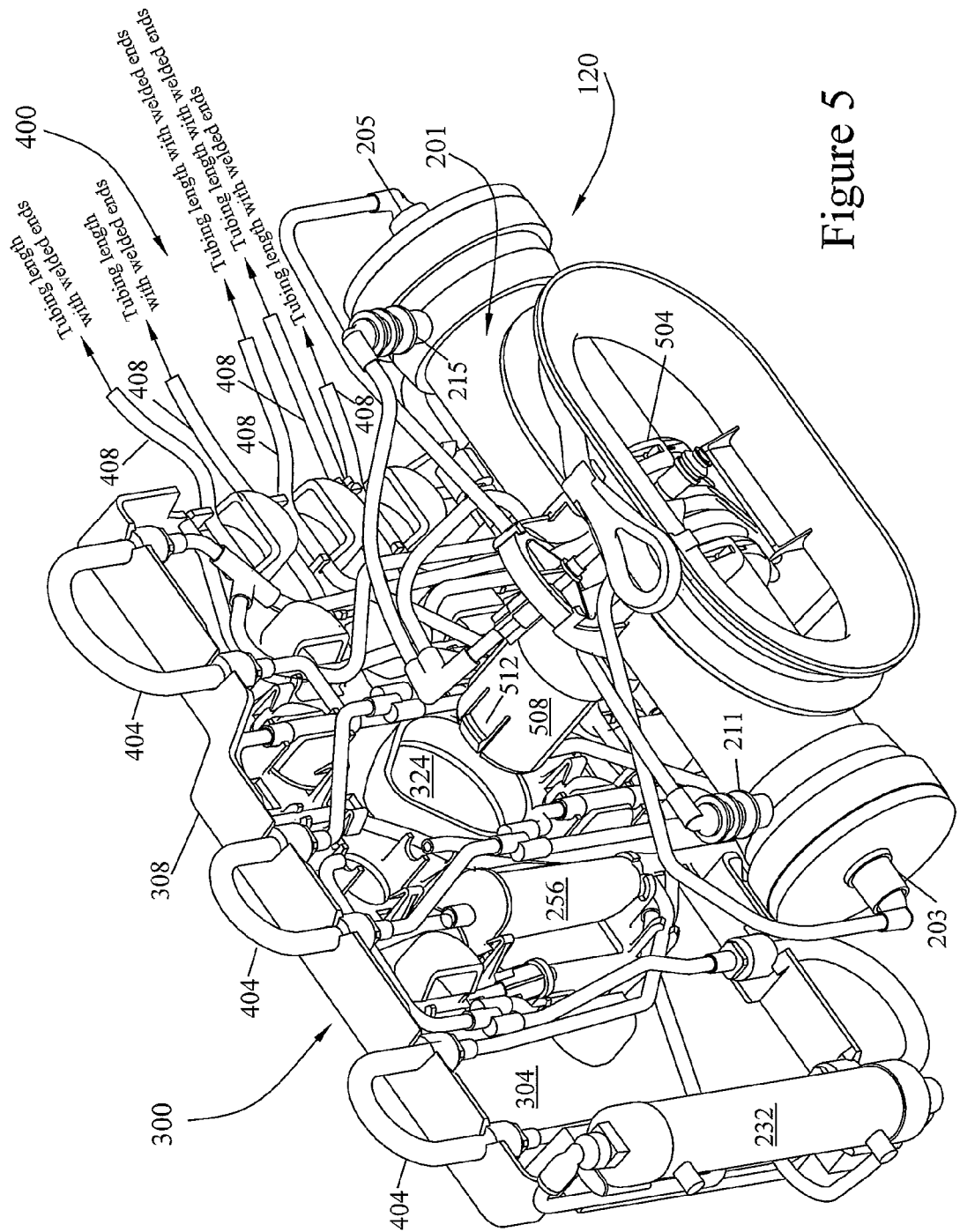
FIG. 5 is a perspective view of a premounted fluid conveyance assembly.

Referring now to FIG. 5, a perspective view of a detachably-attachable premounted fluid conveyance assembly 120 is shown. The premounted fluid conveyance assembly 120 is detachably-attachable to the cell expansion machine 104 to facilitate relatively quick exchange of a new or unused premounted fluid conveyance assembly 120 at a cell expansion machine 104 for a used premounted fluid conveyance assembly 120 at the same cell expansion machine 104. As shown in FIG. 5, the bioreactor 201 is attached to a bioreactor coupling 504 that includes a shaft fitting 508. The shaft fitting 508 includes one or more shaft fastening mechanisms, such as a biased arm or spring member 512 for engaging a shaft (shown in FIG. 6) of the cell expansion machine 104.

Referring still to FIG. 5, the premounted fluid conveyance assembly 120 typically includes tubing 408 and various tubing fittings 412 to provide the fluid paths shown in FIG. 2. Although the various media are typically provided at the site where the cell expansion machine 104 is located, the premounted fluid conveyance assembly 120 typically includes sufficient tubing length to extend to the exterior of the cell expansion machine 104 and to enable welded connections to tubing associated with the media bags.

In at least one embodiment, a plurality of premounted fluid conveyance assemblies 120 are used with a common cell expansion machine 104. Here, the plurality of premounted fluid conveyance assemblies 120 use substantially the same lengths of tubing 408 and commonly sized fluid containing structures, such as the bioreactor 201 and the oxygenator 232, so that the volume of fluid necessary to prime the fluid conveyance system 400 of the premounted fluid conveyance assemblies 120 is substantially constant.

Figure 6:
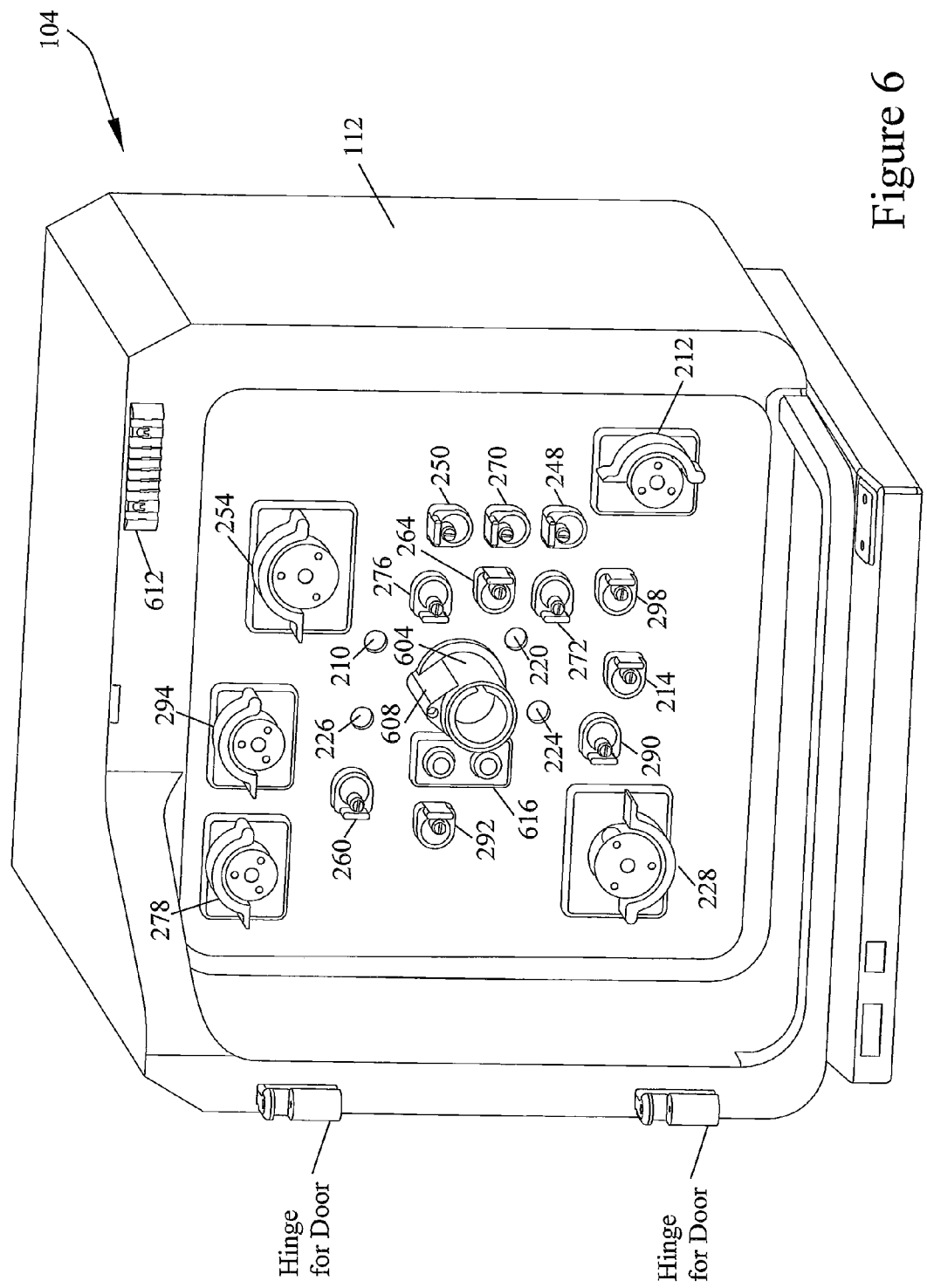
FIG. 6 is a perspective view of a back portion of a cell expansion machine.

Referring now to FIG. 6, the back portion 112 of a cell expansion machine 104 is shown prior to detachably-attaching a premounted fluid conveyance assembly 120. For clarity, the closable door 108 (shown in FIG. 1) is omitted from FIG. 6. The back portion 112 of the cell expansion machine 104 includes a number of different structures for working in combination with elements of a premounted fluid conveyance assembly 120. More particularly, the back portion 112 of the cell expansion machine 104 includes a plurality of peristaltic pumps, including the IC circulation pump 212, the EC circulation pump 228, the IC inlet pump 254, the EC inlet pump 278 and the distribution pump 294. In addition, the back portion 112 of the cell expansion machine 104 includes a plurality of valves, including the IC circulation valve 214, the reagent valve 248, the IC media valve 250, the air removal valve 260, the cell inlet valve 264, the wash valve 270, the distribution valve 272, the EC media valve 276, the IC waste valve 290, the EC waste valve 292, and the harvest valve 298. Several sensors are also associated with the back portion 112 of the cell expansion machine 104, including the IC outlet pressure sensor 210, the combination IC inlet pressure and temperature sensors 220, the combination EC inlet pressure and temperature sensors 224, and the EC outlet pressure sensor 226.

Referring still to FIG. 6, the shaft 604 for rotating the bioreactor 201 is shown. Shaped fitting 608 associated with the shaft 604 allows for proper alignment of the shaft access aperture 324 of the tubing-organizer 300 with the back portion 112 of the cell expansion machine 104. Thus, when an operator of the CES 100 attaches a new or unused premounted fluid conveyance assembly 120 to the cell expansion machine 104, the alignment is a relatively simple matter of properly orienting the shaft access aperture 324 with the shaped fitting 608 and then engaging the pump tubing conduit 404 and tubing 408 with the various corresponding features of the cell expansion machine 104.

Figure 7:
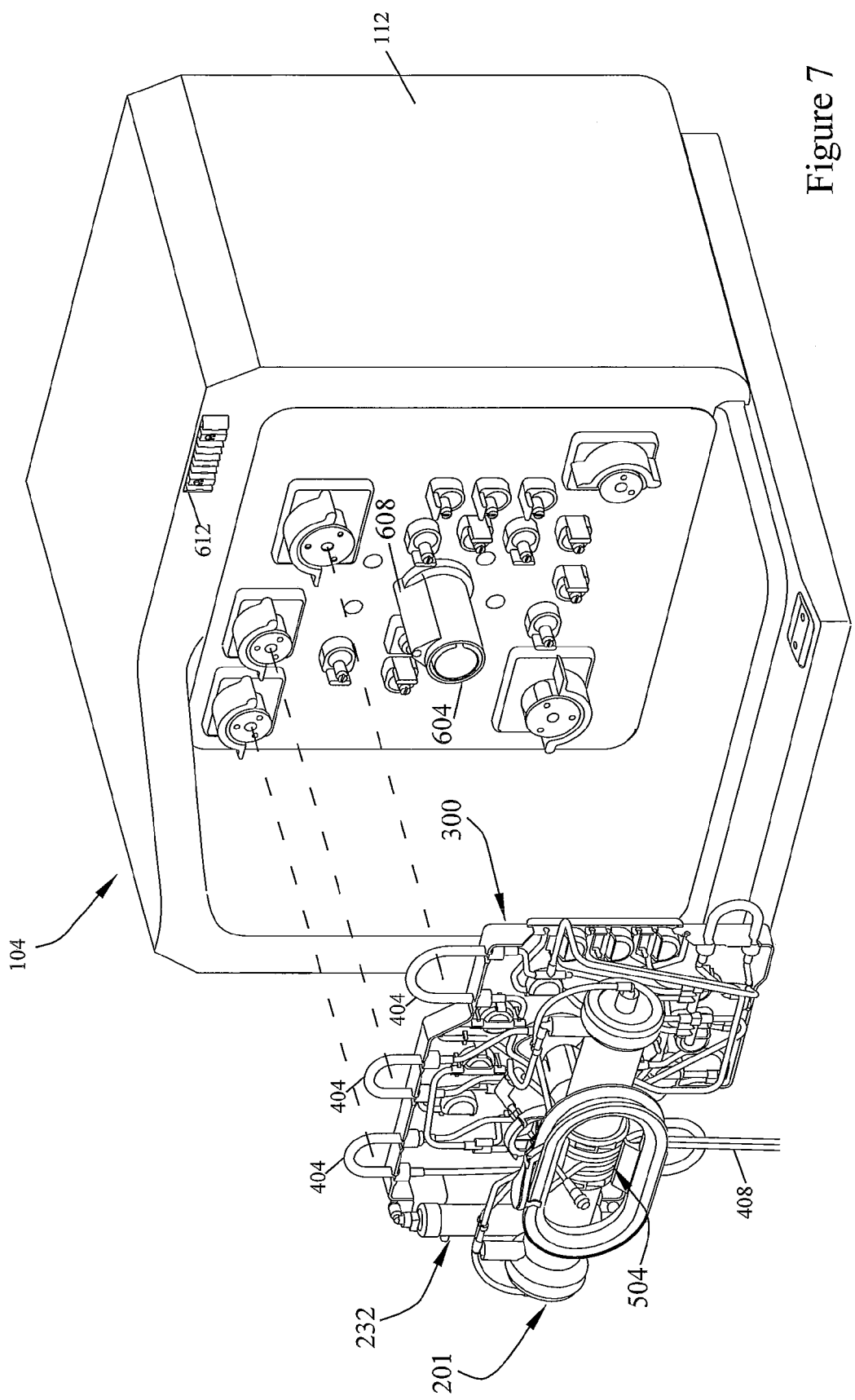
FIG. 7 is an exploded perspective view of a premounted fluid conveyance assembly aligned with the back portion of a cell expansion machine.

Referring now to FIG. 7, a premounted fluid conveyance assembly 120 is shown in spaced alignment with the back portion 112 of a cell expansion machine 104. For clarity, the closable door 108 (shown in FIG. 1) is omitted from FIG. 7. As noted above, the task associated with attaching a premounted fluid conveyance assembly 120 to the back portion 112 of the cell expansion machine 104 includes the operator aligning the shaft access aperture 324 of the tubing-organizer 300 with the shaft 604 and shaped fitting 608 of the back portion 112. The tubing 408 of the premounted fluid conveyance assembly 120 is then manipulated to engage the various valves of the cell expansion machine 104. Similarly, the pump tubing conduit 404 is manipulated to engage the various peristaltic pumps of the cell expansion machine 104. In addition, the sensors associated with the premounted fluid conveyance assembly 120 are aligned with the various sensors associated with cell expansion machine 104.

Still referring to FIG. 7, cell expansion machine 104 preferably includes a plurality of tubing guide slots 612 for exterior access of the tubing 408 to various media. The tubing guide slots 612 are located along the contact area between the closable door 108 and the back portion 112 of the cell expansion machine 104. Accordingly, the tubing guide slots 612 are substantially aligned in a planar manner with the tubing 408 residing on the premounted fluid conveyance assembly 120 when the premounted fluid conveyance assembly 120 has been detachably-attached to the back portion 112 of the cell expansion machine 104.

Figure 8:
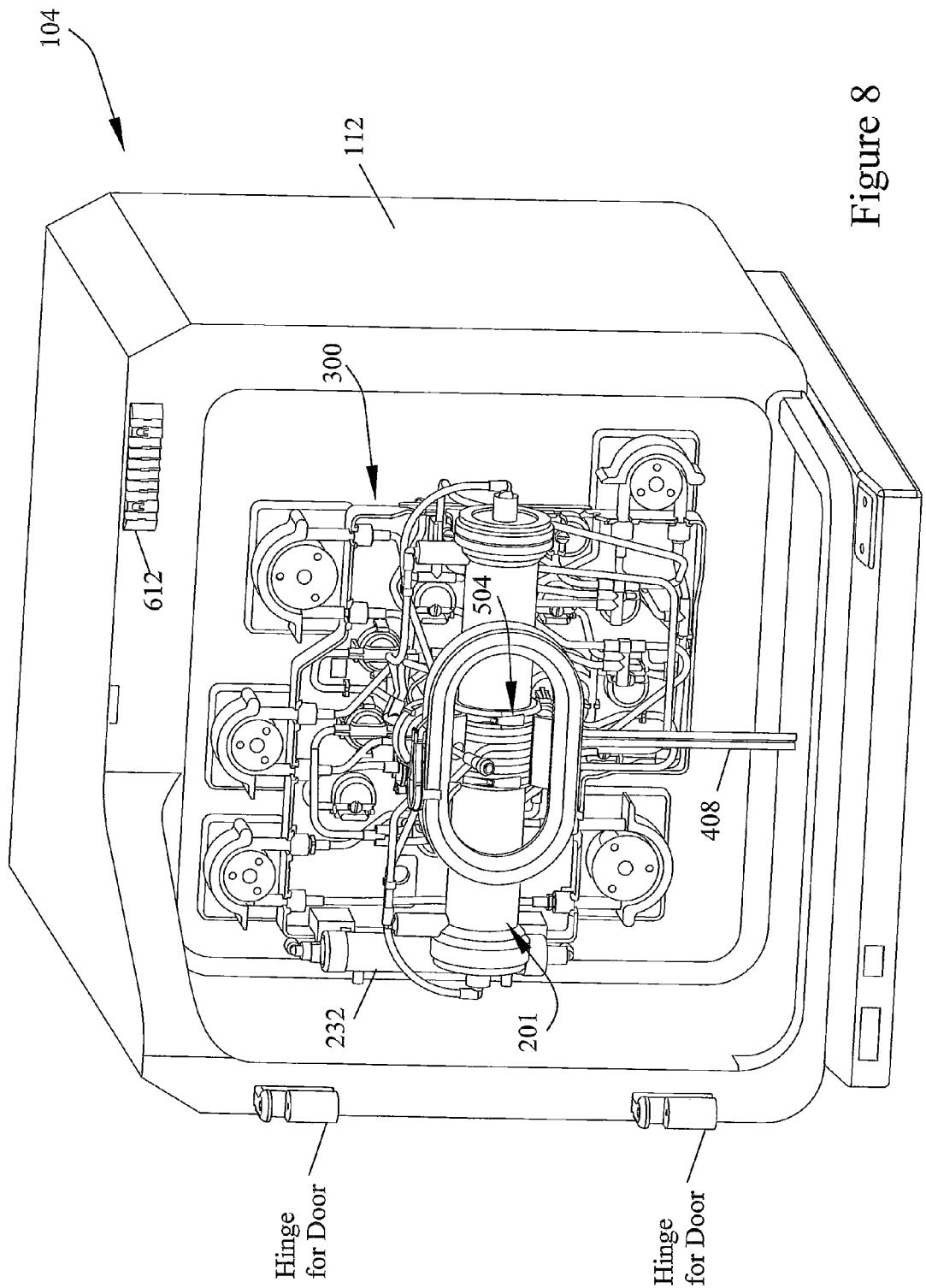
FIG. 8 is a perspective view of a premounted fluid conveyance assembly detachably-attached to the back portion of a cell expansion machine.

At FIG. 8, the premounted fluid conveyance assembly 120 has been attached to the back portion 112 of the cell expansion machine. For clarity, the closable door 108 (shown in FIG. 1) is omitted from FIG. 8. One aspect of the cell expansion machine 104 is to maintain the bioreactor, cells and media at a desirable temperature. Accordingly, the interior space 116 of the cell expansion machine 104 may be temperature controlled. Prior to closing the closable door 108 of the cell expansion machine 104, tubing 408 is passed through the tubing guide slots 612 for exterior access of the tubing 408 to various media. As will be recognized by those skilled in the art, a number of fluid containers (e.g., media bags) can be fluidly associated with the CES 100. By way of example and not limitation, fluids can be attached to the first fluid flow path 206 by welding tubing 408 fluidly associated with the fluid container 262 to the tubing 408 associated with the first fluid flow path 206. A sterile welding device such as a TERUMO® TSCD® Sterile Tubing Welder or other appropriate device may be used.

Figure 9:
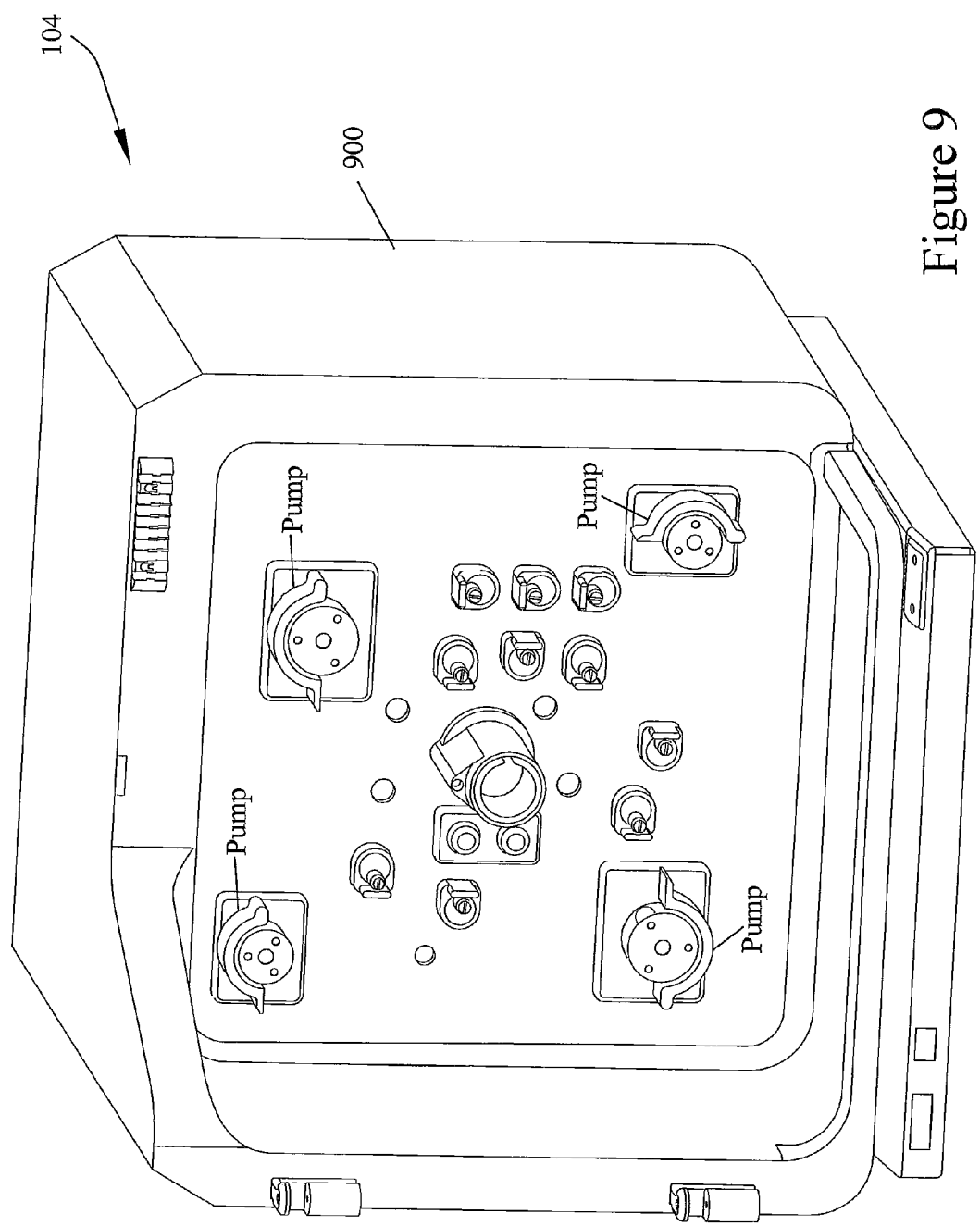
FIG. 9 is an alternative embodiment of a back portion of a cell expansion machine capable of use with an appropriately configured premounted fluid conveyance assembly.

Referring now to FIG. 9, another embodiment of a back portion 900 of a cell expansion machine 104 is shown, wherein the cell expansion machine 104 uses four peristaltic pumps rather than five pumps as described above and shown in FIGS. 1 and 6-8. Accordingly, it is to be understood that the present disclosure and the claims that follow pertain to premounted fluid conveyance assemblies 120 exhibiting tubing configurations and a tubing-organizers 300 suitable for a variety of cell expansion machines 104.

Figure 10:
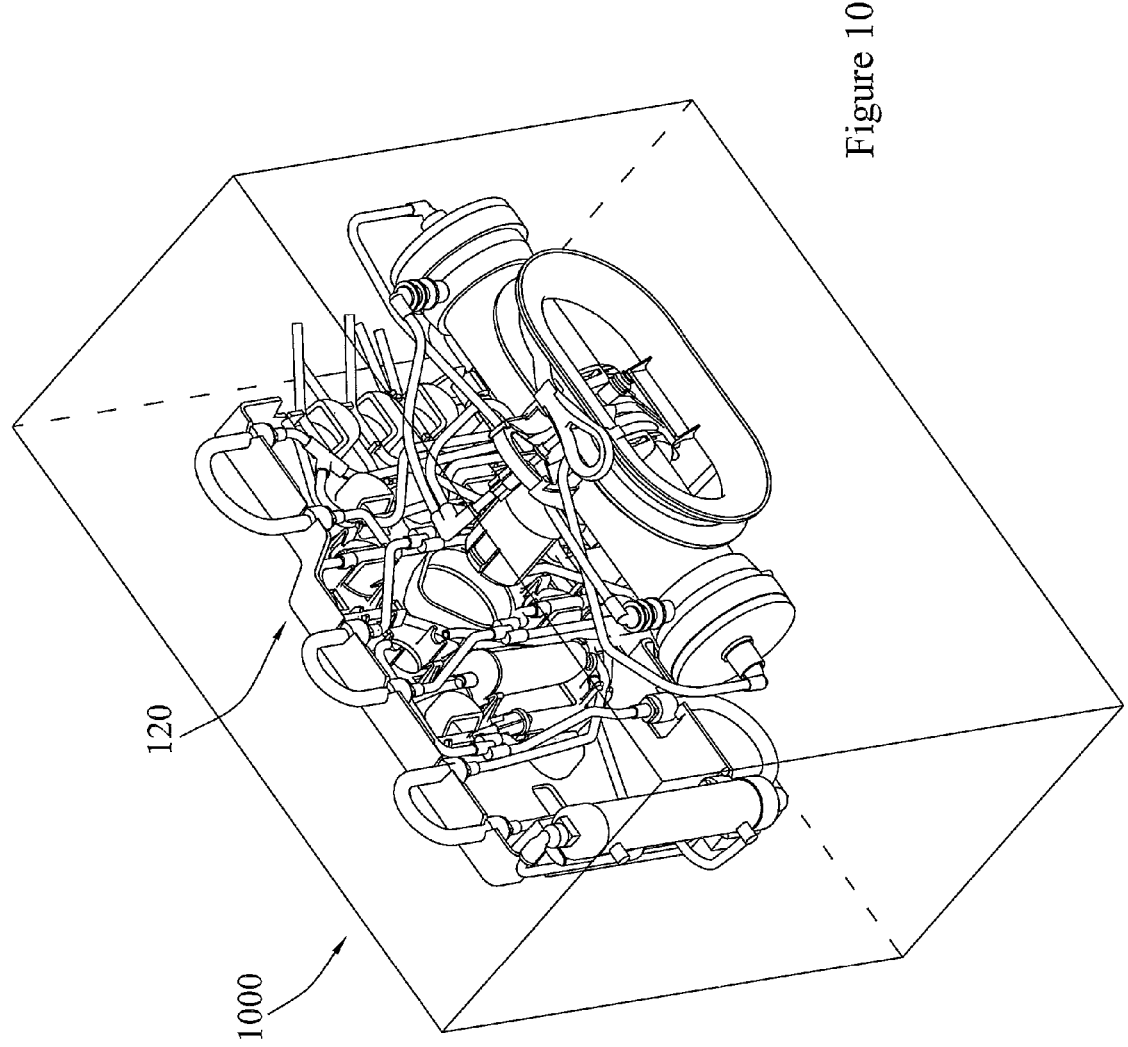
FIG. 10 is a perspective view of a premounted fluid conveyance assembly within an embodiment of sterile packaging.

With reference now to FIG. 10, after manufacturing a premounted fluid conveyance assembly 120, the completed assembly is preferably packaged in a sterile package 1000 for shipment to a facility where the premounted fluid conveyance assembly 120 will be used with a cell expansion machine 104. As those skilled in the art will appreciate, the sterile packaging 1000 may comprise a variety of different forms. As part of the manufacturing and packaging process, the premounted fluid conveyance assembly 120 is sterilized, such as by using ethylene oxide. Accordingly, the premounted fluid conveyance assembly 120 arrives prepackaged and sterile for use by a facility.

Figure 11:
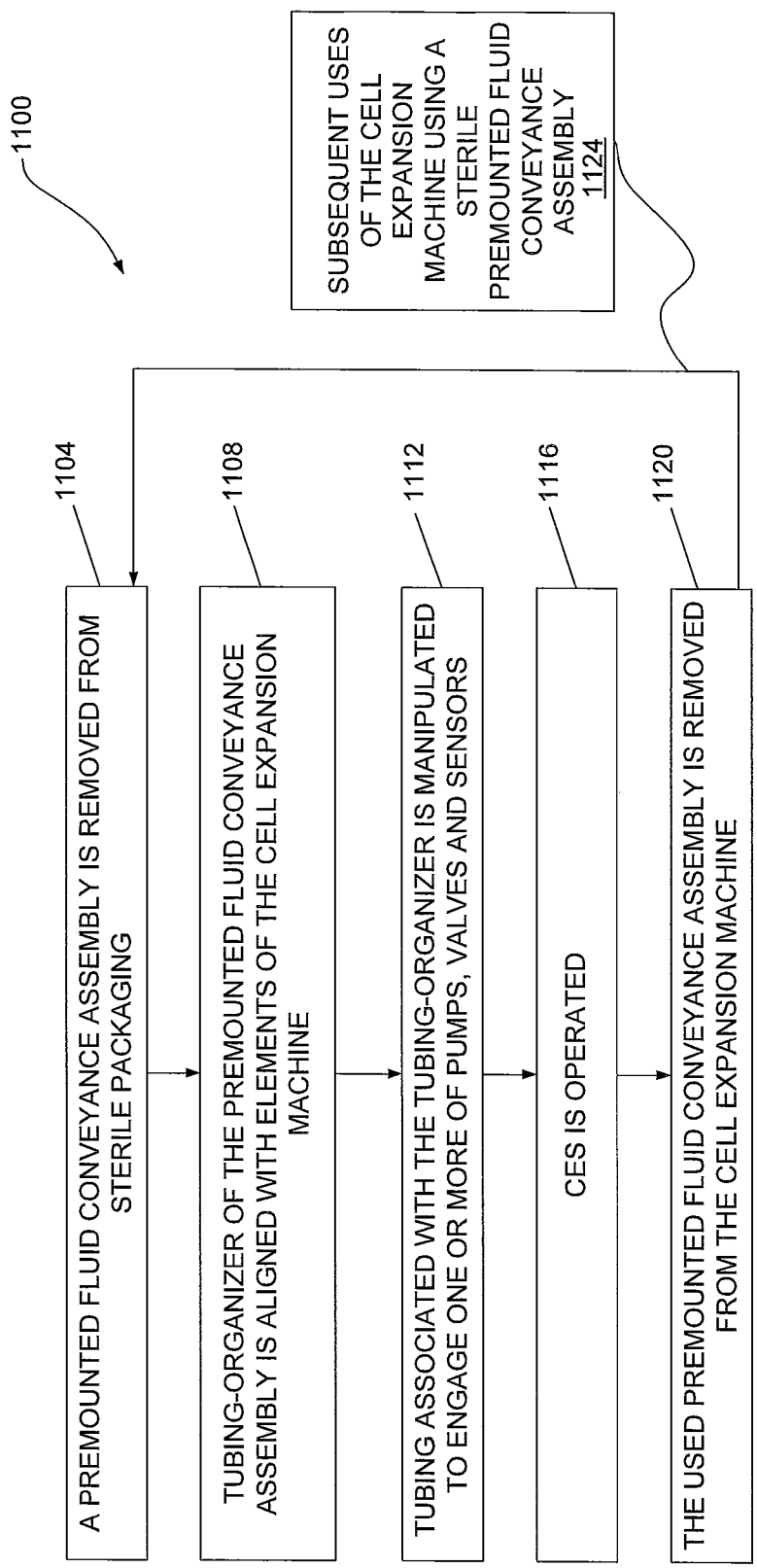
FIG. 11 is a flow chart of a method associated with use of a premounted fluid conveyance assembly.

Referring now to FIG. 11, an exemplary method of use 1100 of one or more premounted fluid conveyance assemblies 120 is described. Accordingly, in at least one embodiment, at 1104 a premounted fluid conveyance assembly 120 is removed from sterile packaging 1000. At 1108, the tubing-organizer 300 is aligned with one or more elements associated with the cell expansion machine 104. By way of example, the shaft access aperture 324 of the tubing-organizer 300 is aligned with the shaped fitting 608 of the shaft 604. At 1112, pump tubing conduit 404 and tubing 408 associated with the premounted fluid conveyance assembly 120 is manipulated to engage one or more of the pumps, valves and sensors of the cell expansion machine 104. In addition, the shaft fitting 508 of the bioreactor coupling 504 is engaged with the shaft 604. At 1116, the cell expansion system 100 is operated to grow and/or expand cells in the bioreactor 201. At 1120, the used premounted fluid conveyance assembly 120 is removed from the cell expansion machine 104. As shown at 1124, subsequent uses of the cell expansion machine 104 can be performed by detachably-attaching another premounted fluid conveyance assembly 120 after a prior used premounted fluid conveyance assembly 120 is removed from the cell expansion machine 104.

In at least one embodiment, a first set of cells is grown and/or expanded in a first premounted fluid conveyance assembly 120 followed by growth and/or expansion of a second set of cells using a second premounted fluid conveyance assembly 120, wherein the cell expansion machine 104 used for growing the first set of cells and the second set of cells is not sterilized between growing the first set of cells and the second set of cells.

As those skilled in the art will appreciate, the used premounted fluid conveyance assembly 120 may be disposed of, such as by incineration, after the used premounted fluid conveyance assembly 120 is removed from the cell expansion machine 104. For the embodiments described herein, fluid circulation paths, including fluid conduit, may be constructed of any appropriate material suitable for the media, cells, and other equipment used. By way of example, one or more different types of tubing may be used in the fluid conveyance system 400. The type of tubing for engaging the peristaltic pumps of the cell expansion machine 104 may be different than the type of tubing associated with the various valves. As one example, fluid flow paths may be constructed of tubing and tubing conduits and operate in conjunction with valves, pumps and other components.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The one or more present inventions, in various embodiments, include components, methods, processes, systems and/or apparatus substantially as depicted and described herein, including various embodiments, subcombinations, and subsets thereof. Those of skill in the art will understand how to make and use the present invention after understanding the present disclosure.

The present invention, in various embodiments, includes providing devices and processes in the absence of items not depicted and/or described herein or in various embodiments hereof, including in the absence of such items as may have been used in previous devices or processes (e.g., for improving performance, achieving ease and/or reducing cost of implementation).

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention (e.g., as may be within the skill and knowledge of those in the art, after understanding the present disclosure). It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A premounted fluid conveyance assembly for use with a cell expansion machine, the premounted fluid conveyance assembly comprising:
    a tubing-organizer comprising an oblong shaped access aperture that is shaped to mate with a fitting on a rotatable shaft of the cell expansion machine, wherein the tubing-organizer further comprises a plurality of sensor ports to provide access between pressure and temperature sensors and sensor couplings;
    a fluid conveyance system at least partially attached to the tubing-organizer, the fluid conveyance system comprising:
        a gas transfer module;
        a length of tubing fluidly associated with the gas transfer module;
        a rotatable hollow fiber bioreactor fluidly associated with the length of tubing and the gas transfer module; and
        a bioreactor coupling comprising a shaft fitting, wherein the bioreactor coupling is coupled to the rotatable hollow fiber bioreactor and the shaft fitting comprises at least a spring member for engaging with the rotatable shaft of the cell expansion machine to rotate the rotatable hollow fiber bioreactor;
        a plurality of pump tubing conduits, at least a portion of each of the plurality of pump tubing conduits extending beyond a support member and looping back to a perimeter of the support member, wherein each of the plurality of pump tubing conduits is engageable with at least one of an IC circulation pump, an EC circulation pump, an IC inlet pump, or an IC inlet pump on the cell expansion machine; and
    wherein the tubing-organizer and the fluid conveyance system are adapted to be detachably-attached to the cell expansion machine.

2. The premounted fluid conveyance assembly of claim 1, wherein the tubing-organizer comprises a plurality of apertures and a plurality of tubing holders spaced across a height and a width of a wall and a perimeter of the tubing-organizer.

3. The premounted fluid conveyance assembly of claim 1, wherein the fluid conveyance system further comprises an air removal chamber.

4. A premounted fluid conveyance assembly for use with a cell expansion machine, the cell expansion machine including at least one valve clamp and a rotatable shaft, the premounted fluid conveyance assembly comprising:
    a fluid conveyance system comprising:
        a gas transfer module;
        a length of tubing fluidly associated with the gas transfer module;
        a rotatable hollow fiber bioreactor fluidly associated with the length of tubing and the gas transfer module;
        a bioreactor coupling comprising a shaft fitting, wherein the bioreactor coupling is coupled to the rotatable hollow fiber bioreactor and the shaft fitting comprises at least a spring member for engaging with the rotatable shaft of the cell expansion machine to rotate the rotatable hollow fiber bioreactor;
        a support member including a plurality of holding elements, the plurality of holding elements including a gas transfer module mounting post and a plurality of tubing guides holding at least a portion of the length of tubing, wherein the support member further comprises a shaft access aperture that is oblong shaped to mate with a fitting on the rotatable shaft of the cell expansion machine and the support member further comprising a plurality of sensor ports to provide access between pressure and temperature sensors and sensor couplings;
        a plurality of pump tubing conduits, at least a portion of each of the plurality of pump tubing conduits extending beyond the support member and looping back to a perimeter of the support member, wherein each of the plurality of pump tubing conduits is engageable with at least one of an IC circulation pump, an EC circulation pump, an IC inlet pump, or an IC inlet pump on a cell expansion machine; and wherein the support member and the fluid conveyance system are adapted to be detachably-attached to the cell expansion machine.

5. The premounted fluid conveyance assembly of claim 4, wherein the support member comprises a valve access opening adapted for allowing contact of the at least one valve clamp with a portion of the length of tubing.

6. The premounted fluid conveyance assembly of claim 4, wherein the fluid conveyance system further comprises an air removal chamber.

7. A premounted fluid conveyance assembly for use with a cell expansion machine, the cell expansion machine including at least one valve clamp, at least one pump, and a rotatable shaft associated within a shaped fitting, the premounted assembly comprising:

a fluid conveyance system comprising:
 a gas transfer module;
 a length of tubing fluidly associated with the gas transfer module;
 a rotatable hollow fiber bioreactor fluidly associated with the length of tubing and the gas transfer module;
 a bioreactor coupling comprising a shaft fitting, wherein the bioreactor coupling is coupled to the rotatable hollow fiber bioreactor and the shaft fitting comprises a spring member for engaging with the rotatable shaft of the cell expansion machine to rotate the rotatable hollow fiber bioreactor;

a means for supporting at least a portion of the fluid conveyance system, wherein the means for supporting comprises:
 a shaped access aperture that is oblong shaped to mate with a fitting on the rotatable shaft of the cell expansion machine;
 a plurality of sensor ports to provide access between pressure and temperature sensors and sensor couplings;
 a means for detachably-attaching the means for supporting to the cell expansion machine;
 a means for holding the gas transfer module; and
 a means for holding the length of tubing fluidly associated with the gas transfer module; and
 a plurality of pump tubing conduits, at least a portion of each of the plurality of pump tubing conduits extending beyond the means for supporting and looping back to a perimeter of the means for supporting, wherein each of the plurality of pump tubing conduits is engageable with at least one of an IC circulation pump, an EC circulation pump, an IC inlet pump, or an IC inlet pump on the cell expansion machine.

8. The premounted fluid conveyance assembly of claim 7, wherein the means for supporting comprises a tubing-organizer.

9. The premounted fluid conveyance assembly of claim 7, wherein the means for holding the length of tubing fluidly associated with the gas transfer module comprises a plurality of tubing guides.

10. The premounted fluid conveyance assembly of claim 7, wherein the means for supporting includes a plurality of apertures spaced across a height and a width of a wall and a perimeter of the means for supporting.

11. The premounted fluid conveyance assembly of claim 7, further comprising a means for guiding a portion of the length of tubing between a back portion and a door of the cell expansion machine.

12. The premounted fluid conveyance assembly of claim 11, wherein the means for guiding comprises a plurality of tubing guide slots.

13. The premounted fluid conveyance assembly of claim 7, wherein the fluid conveyance system further comprises an air removal chamber.

* * * * *